(12) United States Patent
Auld et al.

(10) Patent No.: US 11,801,130 B2
(45) Date of Patent: Oct. 31, 2023

(54) HAPTIC OPTIC MANAGEMENT SYSTEM UTILIZING EDGE ROLLERS

(71) Applicant: Alcon Inc., Fribourg (CH)

(72) Inventors: Jack Robert Auld, Laguna Niguel, CA (US); Matthew Braden Flowers, Aliso Viejo, CA (US); Matthew Douglas Mccawley, San Clemente, CA (US); Andrew Thomas Schieber, Tustin, CA (US); Marcus Antonio Souza, Costa Mesa, CA (US); Sudarshan B. Singh, Euless, TX (US)

(73) Assignee: Alcon Inc., Fribourg (CH)

(*) Notice: Subject to any disclaimer, the term of this patent is extended or adjusted under 35 U.S.C. 154(b) by 689 days.

(21) Appl. No.: 16/720,523

(22) Filed: Dec. 19, 2019

(65) Prior Publication Data

US 2020/0197170 A1 Jun. 25, 2020

Related U.S. Application Data

(60) Provisional application No. 62/782,839, filed on Dec. 20, 2018.

(51) Int. Cl.
*A61F 2/16* (2006.01)
*A61F 2/48* (2006.01)

(52) U.S. Cl.
CPC ............ *A61F 2/1678* (2013.01); *A61F 2/167* (2013.01); *A61F 2/484* (2021.08); *A61F 2002/1683* (2013.01)

(58) Field of Classification Search
CPC ........ A61F 2/1678; A61F 2/167; A61F 2/484; A61F 2002/1683; A61F 2/1691; A61F 9/00736
See application file for complete search history.

(56) References Cited

U.S. PATENT DOCUMENTS

| | | | |
|---|---|---|---|
| 6,143,001 A | 11/2000 | Brown et al. | |
| 6,447,519 B1* | 9/2002 | Brady | A61F 2/1691 606/107 |
| 8,273,122 B2 | 9/2012 | Anderson | |
| 8,753,388 B2 | 6/2014 | Waldock | |
| 9,095,426 B2 | 8/2015 | Ayton et al. | |
| 9,364,320 B2 | 6/2016 | Ichinohe et al. | |
| 9,572,710 B1 | 2/2017 | Kudo et al. | |
| 10,098,730 B2 | 10/2018 | Maroscheck et al. | |
| 10,881,505 B2 | 1/2021 | Glick et al. | |

(Continued)

FOREIGN PATENT DOCUMENTS

JP 5301943 B2 6/2013
JP 6967374 B2 10/2021

*Primary Examiner* — Ashley L Fishback
*Assistant Examiner* — Chima U Igboko

(57) ABSTRACT

Systems, methods, and devices for inserting an intraocular lens (IOL) into an eye may be provided. In an exemplary aspect, the present disclosure is directed to a haptic optic management system. The haptic management system may include a housing that includes a bore and a cavity disposed in a first surface of the housing. The cavity may include a first end portion, a second end portion, and a central portion, wherein the cavity provides access to the bore through the first surface of the housing. The haptic management system may include arms coupled to the housing. The haptic management system may include edge rollers coupled to the housing.

9 Claims, 12 Drawing Sheets

(56) References Cited

U.S. PATENT DOCUMENTS

| | | |
|---|---|---|
| 11,026,780 B2 | 6/2021 | Maroschek |
| 2005/0033308 A1* | 2/2005 | Callahan ................. A61F 2/167 |
| | | 606/107 |
| 2009/0318933 A1 | 12/2009 | Anderson |

* cited by examiner

HAPTIC OPTIC MANAGEMENT SYSTEM UTILIZING EDGE ROLLERS

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded natural lens with an intraocular lens ("IOL"). A large incision site may cause a longer post-operation healing time. To reduce this healing time, typical operating procedures have shifted to making incisions of about 2 millimeters in size into the eye. While this smaller size of incision may reduce post-operation healing time, problems such as the size and functionality of the insertion tool may arise as the incision size continues to shrink. Typically, the insertion tool may be pre-loaded with the IOL that may be inserted into the patient's eye once the clouded natural lens is removed. The insertion tool may include a plunger for forcing the IOL out of the nozzle of the insertion tool. The plunger may have additional functions including haptic tucking and folding of the IOL. Once an incision has been made, the insertion tool may be inserted into the eye through the incision, and the folded IOL may be dispensed into the eye by actuation of the plunger. As the incision site decreases, the size of the nozzle of the insertion tool may decrease accordingly.

SUMMARY

In an exemplary aspect, the present disclosure is directed to a haptic optic management system. The haptic management system may include a housing that includes a bore and a cavity disposed in a first surface of the housing. The cavity may include a first end portion, a second end portion, and a central portion, wherein the cavity provides access to the bore through the first surface of the housing. The haptic management system may include arms coupled to the housing. The haptic management system may include edge rollers coupled to the housing.

In another exemplary aspect, the present disclosure is directed to an insertion tool. The insertion tool may include a drive system, wherein the drive system includes a body. The insertion tool may further include a plunger disposed at least partially in the drive system. The insertion tool may further include a nozzle. The insertion tool may further include a haptic optic management system disposed between the drive system and the body. The haptic optic management system may include a housing include a bore and a cavity disposed in a first surface of the housing. The cavity may include a first end portion, a second end portion, and a central portion, wherein the cavity provides access to the bore through the first surface of the housing. The haptic management system may include arms coupled to the housing. The haptic management system may include edge rollers coupled to the housing.

In yet another exemplary aspect, the present disclosure is directed a method of delivering an intraocular lens. The method may include rotating a pair of arms such that each of the arms engages a corresponding haptic extension of an intraocular lens, thereby moving the haptic extension up inclined surfaces and onto an optic of the intraocular lens. The method may further include pivoting a pair of edge rollers in engagement with edges of the intraocular lens to cause the optic to fold in upon itself and move the intraocular lens into alignment with a bore. The bore may extend from a first end of a housing to a cavity formed in a first surface of the housing in which the intraocular lens is disposed. The method may further include actuating a drive system to dispense the intraocular lens from the bore, through a nozzle, and into an eye, wherein the nozzle is coupled to the housing.

The different aspects may include one or more of the following features. The bore may include a first portion that has a U-shaped cross-section and extends from a first end of the housing to the central portion of the cavity. The bore may include a second portion that has a smaller cross-section than the first portion and extends from the central portion of the cavity to a second end of the housing. The haptic optic management system may further include an intraocular lens disposed in the cavity, wherein the intraocular lens includes an optic and haptic extensions that extend from the optic. One of the haptic extensions may from the optic onto the first end portion. Another of the haptic extensions may from the optic onto the second end portion. The first end portion and the second end portion may each include an end wall, a raised platform adjacent to the end wall for supporting one of the arms, a portion adjacent to the raised platform for supporting for haptic extension of an intraocular lens, and inclined surface adjacent to the portion. The arms may include a pair of arms, wherein one of the pair of the arms is disposed in the first end portion, and another of the pair of the arms is disposed in the second end portion. The arms may each include a first portion, a second portion joined to the first portion at a bend, a pin extending from the second portion, and a tab extending from the first portion. Rotating the arms may include applying an external force to a tab that extends from each of the arms. The arms may each be rotatable about the respective second portion. The edge rollers may each include a pair of the edge rollers, wherein each of the pair of the edge rollers are disposed on opposite platforms formed on either side of the central portion of the cavity. The edge rollers may each include a slot formed in a first surface for receiving an edge of an optic of an intraocular lens, a bore formed adjacent the slot, and a tab extending on a second surface opposite the first surface, wherein the tab is received in a slot formed in a sidewall of the housing. The tab may be received in a slot formed in a sidewall of the housing. Pivoting the edge rollers may include applying an external force to the tab that extends from each of the edge rollers to cause each of the edge rollers to pivot in an arc. The plunger of the insertion tool may be operable to engage the intraocular lens when the drive system is actuated to dispense the intraocular lens from the nozzle. The drive system of the insertion tool may include a lever and a pneumatic system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
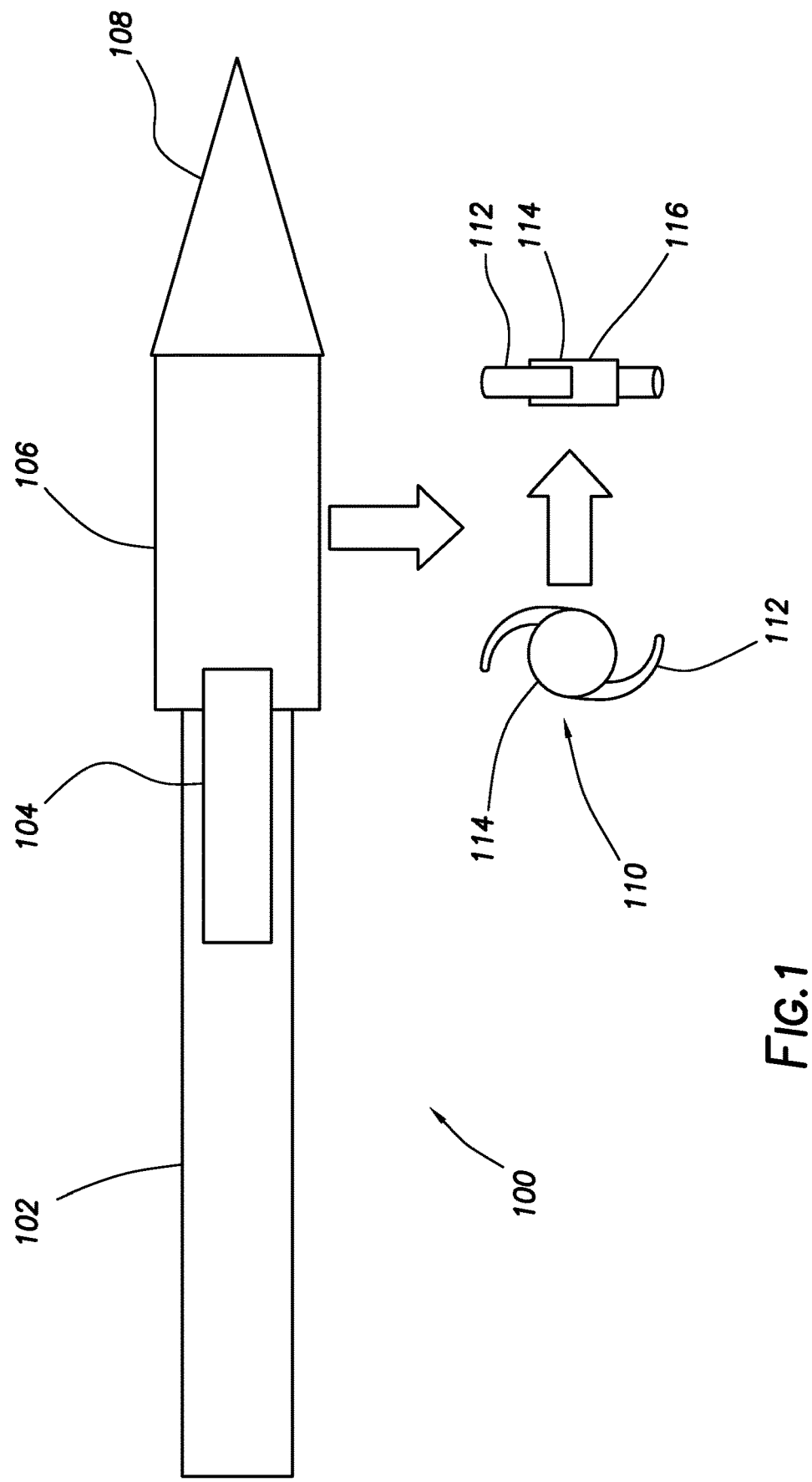
FIG. 1 illustrates a schematic of an example insertion tool operable to deliver an IOL into an eye.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers may be used throughout the drawings to refer to the same or like parts.

The example embodiments described herein generally relate to eye surgery. More particularly, the example embodiments generally relate to systems, methods, and devices for inserting an intraocular lens ("IOL") into an eye. Embodiments may include an insertion tool for preparation and delivery of the IOL into a patient's eye that includes a plunger, a nozzle, and a haptic optic management system. In some embodiments, the haptic management system may fold the IOL assembly and tuck one or more haptics of the IOL assembly. The haptic extends from an optic of the IOL and stabilizes the IOL when disposed within the capsular bag of the eye. After preparation of the IOL, the plunger forces the IOL through the insertion tool and out the nozzle.

FIG. 1 illustrates a schematic of an insertion tool 100. In some embodiments, insertion tool 100 may include a drive system 102, a plunger 104, a haptic optic management system (interchangeably referred to as "HOMS") 106, and a nozzle 108. The drive system 102 may be any system or combination of components operable to actuate the plunger 104. For example, the drive system 102 may utilize a lever and/or pneumatic systems; a manually driven system or component; a hydraulic system; or other device operable to drive the plunger 104 to advance; partially advance; or fully deliver an IOL from the insertion tool 100. The plunger 104 may be coupled to the drive system 102. The drive system 102 may be operable to actuate the plunger 104. For example, the drive system 102 may be powered by, for example, electrically, mechanically, hydraulically, pneumatically, combinations thereof, or in some other manner. In response to the drive system 102, the plunger 104 moves through the HOMS 106. The HOMS 106 may be located between the drive system 102 and the nozzle 108. In alternate embodiments, the HOMS 106 may be disposed at other locations within the insertion tool 100. In some embodiments, the HOMS 106 may contain an IOL 110 in an unfolded position.

The drive system 102 may be any system, component, or group of components operable to advance an IOL 110 through the insertion tool 100. For example, the drive system 102 include plunger, schematically shown as plunger 104 in FIG. 1, that is operable to engage an IOL 110 disposed within the insertion tool 100 and advance the IOL 110 within the insertion tool 100. In some instances, the plunger 104 is operable to expel the IOL 110 from the insertion tool 100.

In some embodiments, the drive system 102 may be a manually driven system. That is, in some embodiments, a user applies a force to cause the drive system 102 to operate. An example drive system 102 includes a plunger 104 that is manually engageable directly or indirectly by a user to push the plunger 104 through the insertion tool 100. When advanced, the plunger 104 engages an IOL 110 and advances the IOL 110 through the insertion tool 100, which may also include expelling the IOL 110 from the insertion tool 10. A non-limiting example of a manual IOL insertion tool is shown in U.S. Patent Application Publication No. 2016/0256316, the entire contents of which are incorporated herein by reference in its entirety. According to other implementations, the drive system 102 may be an automated system. Example automated drive systems are shown in U.S. Pat. Nos. 8,808,308; 8,308,736; and 8,480,555, the entire contents of each being incorporated herein by reference in their entirety. Still further, other automated drive systems within the scope of the present disclosure are described in U.S. Pat. No. 8,998,983 and U.S. Patent Application Publication No. 2017/0119522, the entire contents of each being incorporated herein by reference in its entirety. While example drive systems are provided as examples, these systems are not intended to be limiting. Rather, any component, group of components, systems, devices, mechanisms, or combinations thereof operable to advance an IOL 110 is within the scope of the present disclosure.

As shown in FIG. 1, the IOL 110 is a single piece IOL that includes an optic 114 and haptic extensions 112 extending from opposing sides of the optic 114. For example, in the example IOL 110 shown in FIG. 1, the haptic extensions 112 are disposed 180° relative to each other along an outer periphery of the optic 114. However, other types of IOLs are within the scope of the disclosure. For example, a multi-piece IOL, in which the optic 114 and one or more haptic extensions 112 are separate components, may also be used.

Figure 2A:
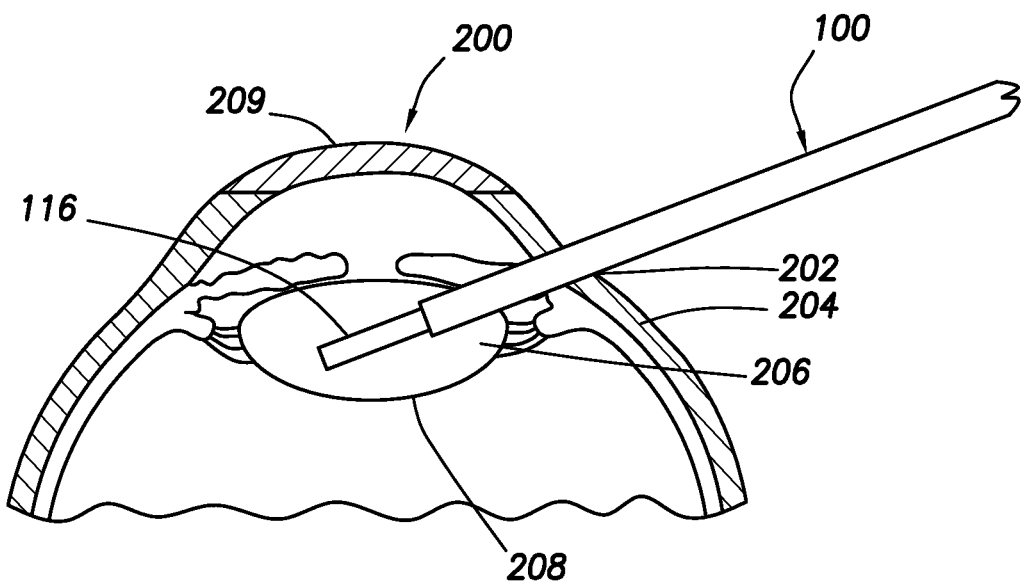
FIG. 2A illustrates an eye in which an IOL is being introduced from an insertion tool.

The IOL 110 may have a shape similar to that of a natural lens of an eye (e.g., eye 200 shown in FIG. 2A). The IOL 110 may be made from a numerous materials including, but not limited to, silicone, acrylic, and/or combinations thereof. Other materials are also contemplated. The haptic extensions 112 extend from a periphery of the optic 114 and function to stabilize the IOL 110 when disposed within an eye.

In some instances, the HOMS 106 may be actuated to tuck the haptic extensions 112 over the optic 114 and fold the optic 114. For example, the HOMS 106 may operate to fold the haptic extensions 112 over the optic 114 and fold the optic 114 over or around the folded haptic extensions 112. The IOL 110 is shown in a folded configuration at 116. The folded IOL 116 may involve one or more haptic extensions 112 folded relative to the optic 114 and, in some instances, the optic 114 folded relative to one or more of the haptic extensions 112. The plunger 104 may be advanced through the HOMS 106 once the HOMS 106 has folded the IOL 110. As the plunger 104 moves through the HOMS 106, the plunger 104 displaces the folded IOL 16 from the HOMS 106. For example, the plunger 104 may force the folded IOL 116 into and through the nozzle 108.

FIG. 2A illustrates an eye 200 of a patient undergoing an operation with insertion tool 100. As illustrated, the insertion tool 100 dispenses a folded IOL 116 into the eye 200 of a patient. In some embodiments, an incision 202 is made in the eye 200 by a surgeon, for example. For example, in some instances, the incision 202 may be made through the sclera 204 of the eye 200. In other instances, an incision may be formed in the cornea 209 of the eye 200. The incision 202 may be sized to permit insertion of a portion of the insertion tool 100 in order to deliver the folded IOL 116 into the capsular bag 208. For example, in some instances, the size of the incision 202 may have a length less than about 2000 microns (2 millimeters). In other instances, the incision 202 may have a length of from about 0 microns to about 500 microns; from about 500 microns to about 1000 microns; from about 1000 microns to about 1500 microns; or from about 1500 microns to about 2000 microns.

Figure 2B:
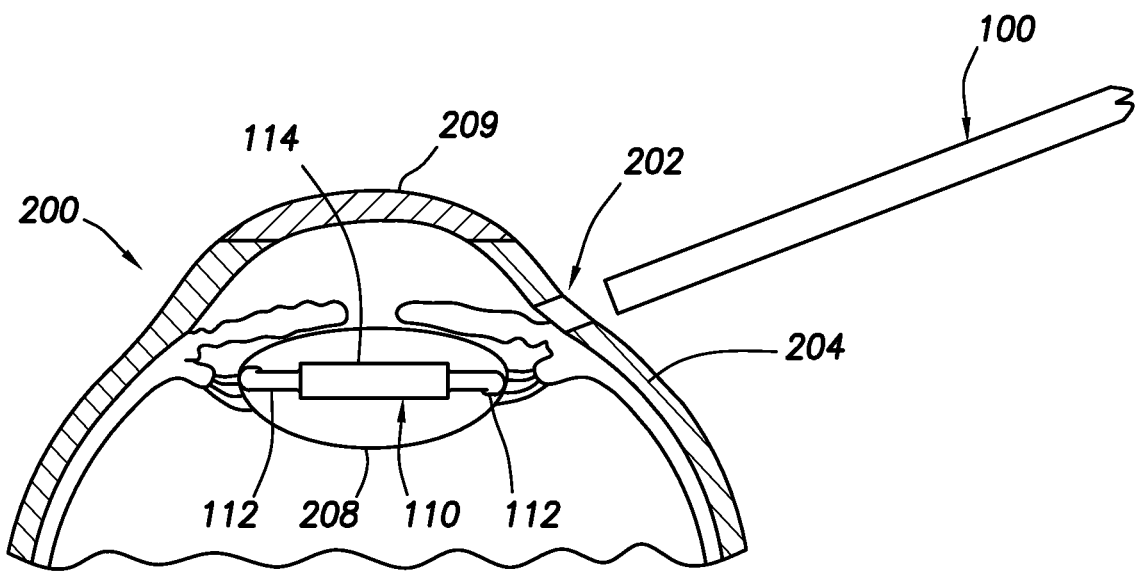
FIG. 2B illustrates the eye shown in FIG. 2A in which the IOL is positioned within the capsular bag of the eye and the insertion tool removed from the eye.

After the incision 202 is made, the insertion tool 100 is inserted through the incision into an interior portion 206 of the eye 200. The insertion tool 100 is actuated to dispense the folded IOL 116 into the capsular bag 208 of the eye 200. Upon dispensation, the folded IOL 116 reverts to an initial, unfolded state, and the IOL 110 settles within the capsular bag 208 of the eye 200, as shown on FIG. 2B. The capsular bag 208 holds the IOL 110 within the eye 200 in a relationship relative to the eye 200 so that the optic 114 refracts light directed to the retina (not shown). The haptic extensions 112 of the IOL 110 engage the capsular bag 208 to secure the IOL 110 therein. After dispensing the IOL 110 into the capsular bag 208, the insertion tool 100 is removed from the eye 200 through the incision 202, and the eye 200 is allowed to heal over a period of time.

Figure 3:
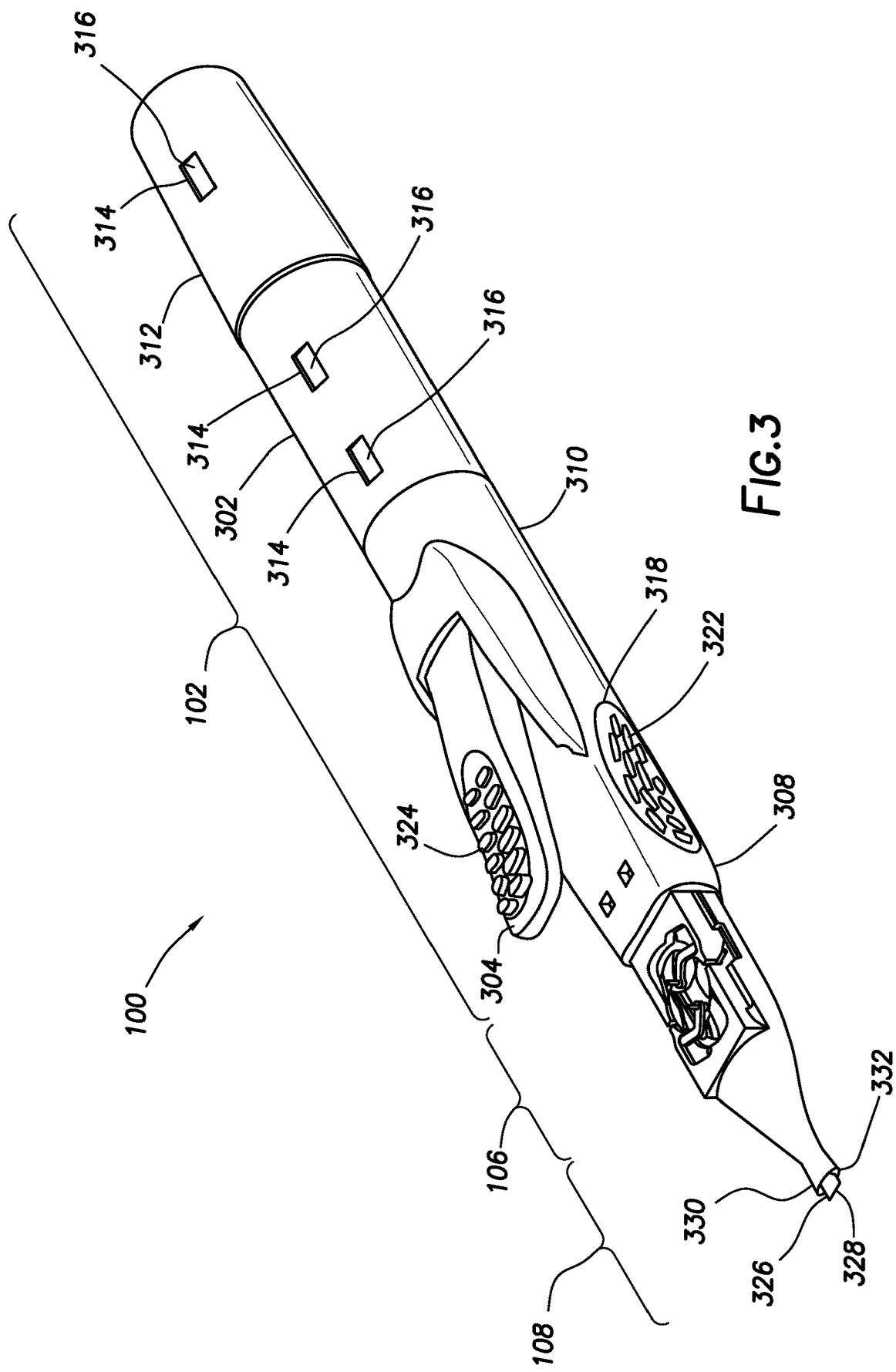
FIG. 3 illustrates a perspective view of another example insertion tool operable to delivery an IOL into an eye.
Figure 4:
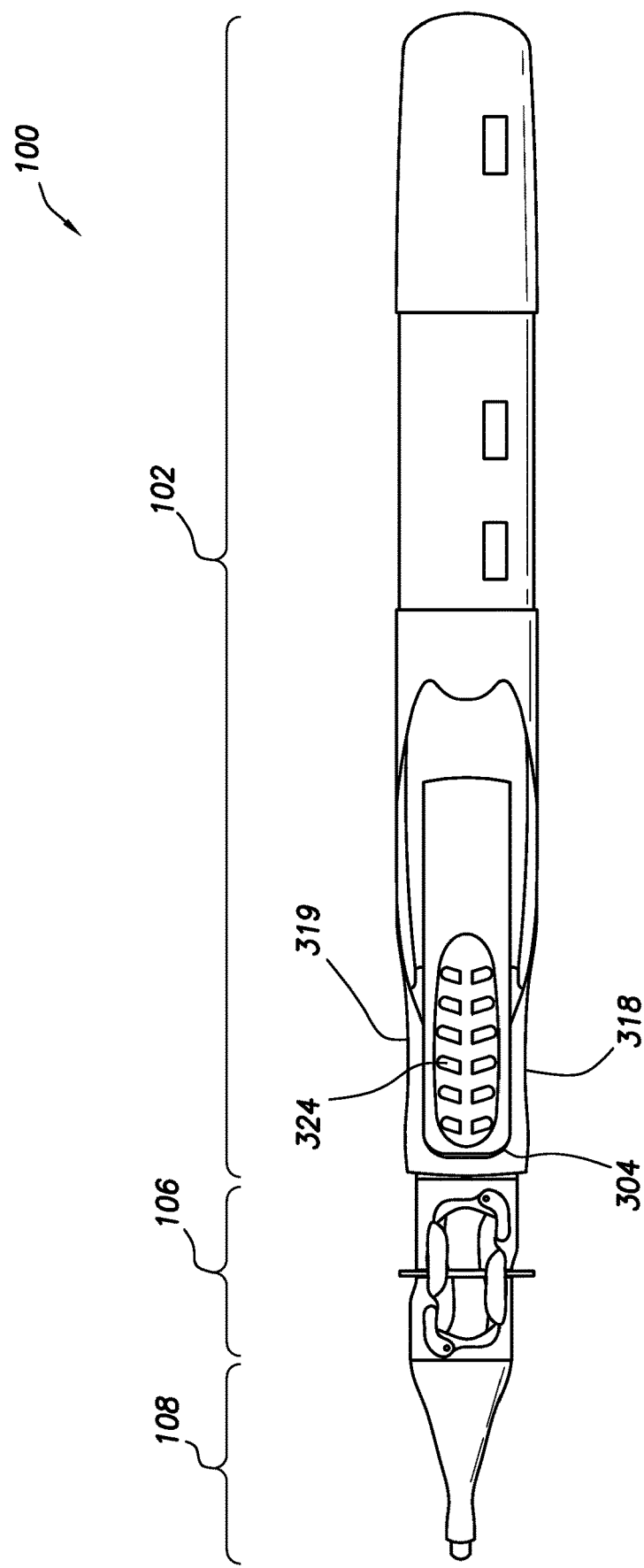
FIG. 4 illustrates a top view of the insertion tool of FIG. 3.
Figure 5:
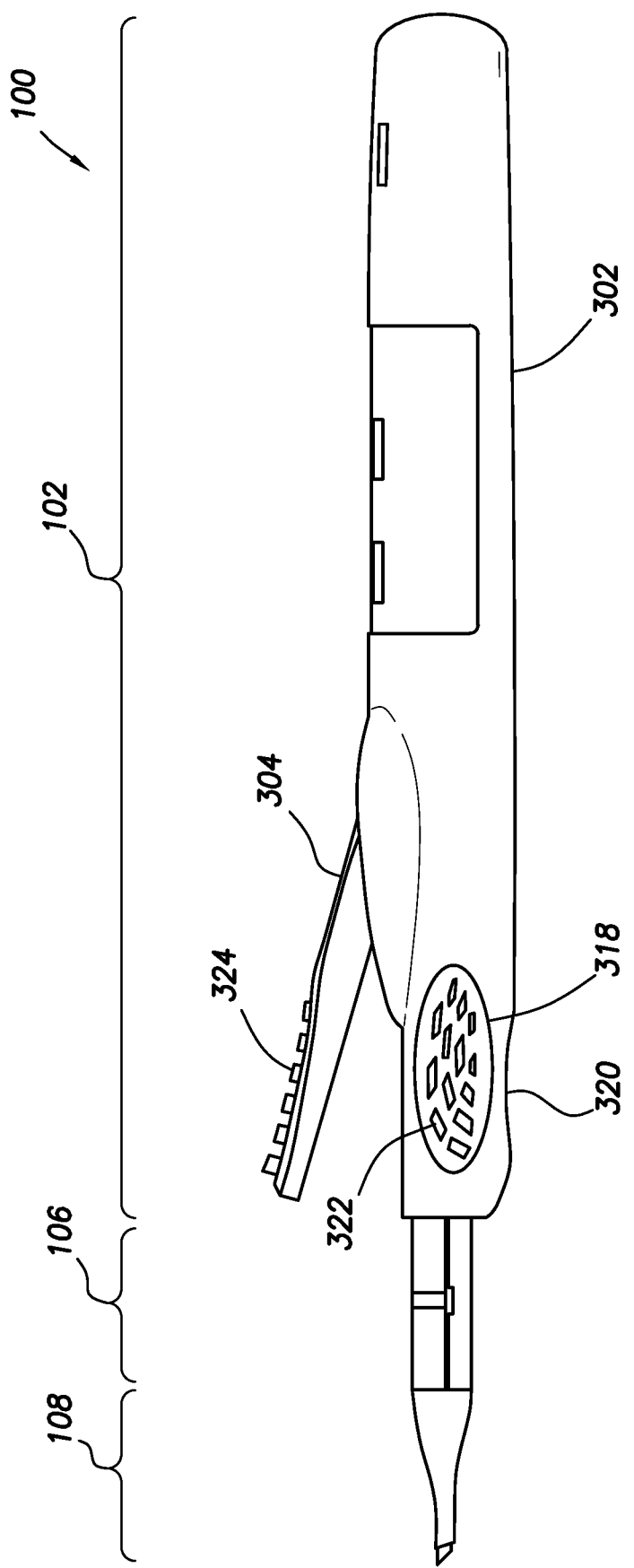
FIG. 5 illustrates a side view of the insertion tool of FIG. 3.

FIGS. 3-5 illustrate an example insertion tool 100 operable to deliver an IOL into the eye. As illustrated, the insertion tool 100 includes a drive system 102, a haptic optic management system 106, and a nozzle 108. The insertion tool 100 may also include a plunger, which may be similar to the plunger 104 shown in FIG. 1. In some instances, the plunger may be actuated to advance an IOL, e.g., which may be similar to the IOL 110 shown in FIG. 1, within the insertion tool 100 and, in some cases, dispense the IOL 110 from the insertion tool 100.

Referring to FIG. 3, the drive system 102 includes a body 302 and a lever 304 that may be pivotally coupled to the body 302. The nozzle 108 is coupled to a distal end 308 of the body 302. The HOMS 106 is disposed between the body 302 and the nozzle 108. In some instances, the nozzle 108 may be integrally connected to the body 302. In other instances, the nozzle 108 may be separate from the body 302 and may be coupled to the body 302 via an interlocking relationship. In some instances, the HOMS 106 and the nozzle 108 may be integrally formed. In other instances, the HOMS 106, the nozzle 108, and the body 302 may be integrally formed.

In some instances, the body 302 may have a slender, elongated shape. In some instances, the body 302 may have a first portion 310 and a second portion 312. In some instances, the first portion 310 and the second portion 312 join along a longitudinally extending interface. In the example shown, the first portion 310 includes a plurality of apertures 314. A plurality of tabs 316 formed on the second portion 312 may be received into the apertures 314 to join the first portion 310 and the second portion 312. The tabs 316 may form an interlocking fit with the apertures 314. However, the construction of the body 302 of the example insertion tool 100 shown in FIGS. 3-5 is merely a non-limiting example. In some instances, the body 302 may be a single unitary piece. In some instances, the body 302 may include one or more cylindrical pieces. Moreover, the body 302 may be constructed in any desirable manner from any number of components.

With continued reference to FIGS. 3-5, the body 302 also includes reliefs 318, 319, and 320. The reliefs 318, 319, and 320 are shallow recesses formed in the body 302 to accommodate, for example, one or more fingers of a user. One or more of the reliefs 318, 319, and 320 may include a textured surface 322 that may provide a user with an improved grip of and control over the insertion tool 100. As shown in FIGS. 3 and 5, the relief 318 may include texture surface 322. However, the scope may not be so limited. Rather any, all, or none of the reliefs 318, 319, and 320 may include the textured surface 322. Similarly, the lever 304 may also include a textured surface 324. However, in some instances, the lever 304 may not include a textured surface.

Referring to FIG. 3, the nozzle 108 includes a distal tip 326 that defines an opening 328. The nozzle 108 also includes a flared portion or wound guard 330. The distal tip 326 may be adapted to be inserted into an incision formed in an eye, such as the incision 202 shown on FIG. 2, in order to deliver a folded IOL there into. The wound guard 330 may include an end surface 332 operable to contact an exterior surface in order to limit a depth to which the distal tip 326 penetrates the eye. In some embodiments, the wound guard 330 may be omitted.

In some embodiments, the insertion tool 100 may be preloaded. That is, the insertion tool 100 may include an IOL disposed therein when provided to an end user. In some instances, the IOL may be disposed within the insertion tool 100 in an unfolded state and ready to be delivered into a patient. Having the insertion tool 100 preloaded with an IOL reduces the number of steps a user must perform both before delivering the IOL into a patient. For example, an insertion tool 100 that is preloaded obviates any steps a user would otherwise be required to perform in order to load the insertion tool 100 with the IOL. With a reduced number of steps, error and risk associated with delivery of the IOL into a patient may be reduced. Further, an amount of time required to deliver the IOL may also be reduced. In some embodiments, the IOL may be pre-loaded into the HOMS 106.

Figure 6:
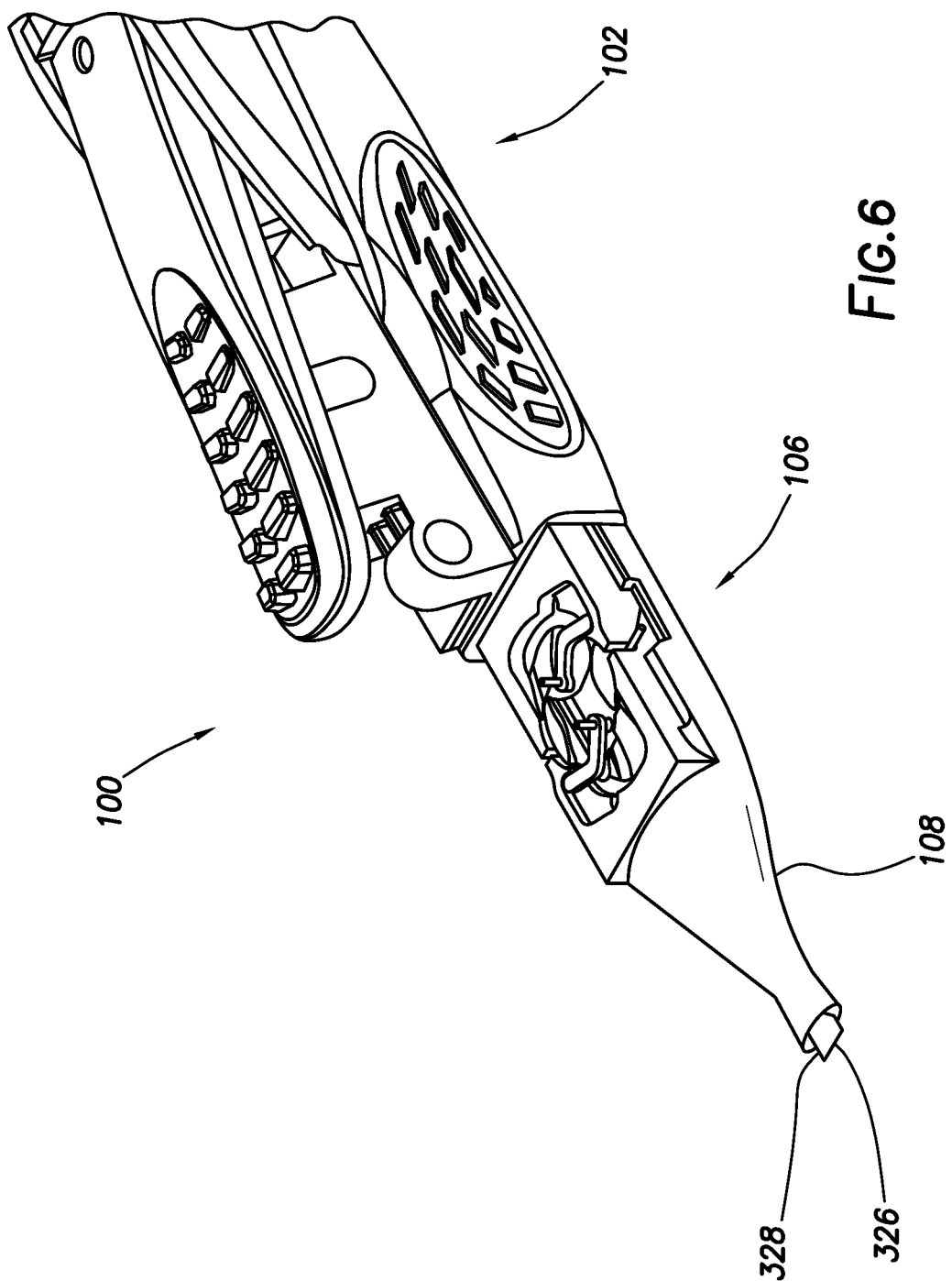
FIG. 6 is a detail view of a distal end of the insertion tool of FIG. 3.

FIG. 6 illustrates a close-up view of an example insertion tool 100 with a haptic optic management system 106. As previously described, the HOMS 106 is operable to fold the IOL (e.g., IOL 110 shown on FIG. 1). For example, in some instances, the HOMS 106 may be operable to fold an IOL 110 from an unstressed condition to a fully folded configuration, as shown in FIG. 1, for example. During folding, the HOMS 106 may tuck or fold the haptic extensions 112 over the optic 114 of the IOL 110 as well as fold edges of the optic 114 over the tucked haptic extensions 112, capturing the haptic extensions 112 and thereby placing the IOL 110 into the folded configuration, as shown in FIG. 1, for example.

As shown in FIGS. 3-6, for example, the HOMS 106 is sized to commensurate with a size of the insertion tool 100. That is, the HOMS 106 has a compact size to avoid or limit an amount of obstruction to a surgeon's view while inserting an IOL into an eye. However, the scope of the disclosure is not so limited. Rather, in some instances, a size and/or shape of the haptic optic management system may be selected to be any desired size or shape. Further, while the HOMS 106 is shown disposed at the distal end of the insertion tool 100, the haptic optic management system 106 may be disposed anywhere within or along the insertion tool 100. In some embodiments, the HOMS 106 may be disposed between the nozzle 108 and the drive system 102.

In the illustrated example of FIGS. 3-6, the HOMS 106 is disposed between the distal end 308 of the body 302 and the nozzle 108. In some instances, the HOMS 106 may be removably coupled to the nozzle 108 and/or the drive system 102. For example, the HOMS 106 may be removably coupled to the body 302 with the use of fasteners or adhesives. In still other implementations, the HOMS 106 may couple to the body 302 by a snap-fit engagement or any other desired method of connection. Without limitation, example fasteners may include nuts and bolts, washers, screws, pins, sockets, rods and studs, hinges and/or any combination thereof.

Figure 7:
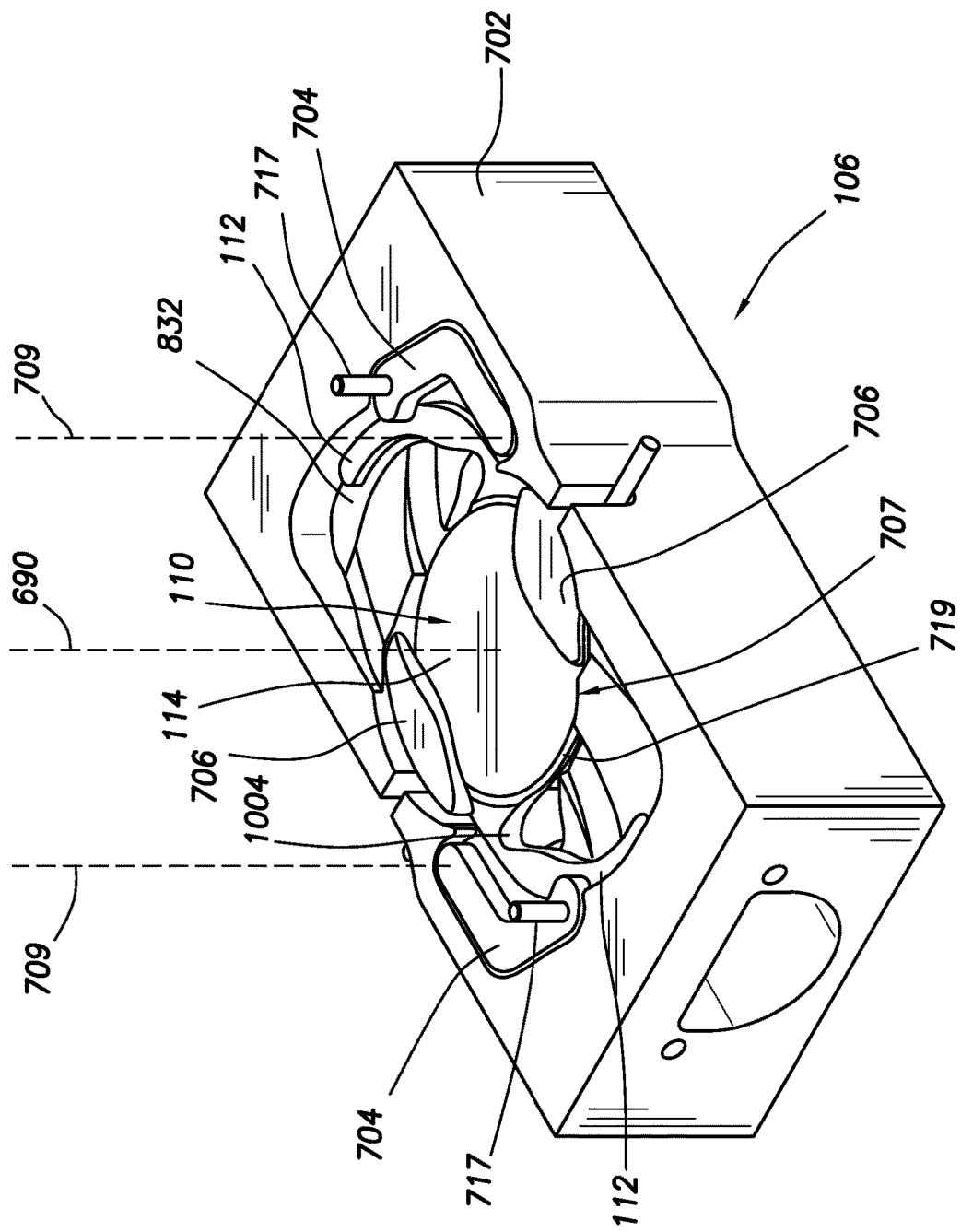
FIG. 7 illustrates an example haptic optic management system that includes edge rollers.

FIG. 7 illustrates an example haptic optic management system 106. In the illustrated example, the HOMS 106 includes a housing 702, arms 704, and edge rollers 706. The housing 702 forms a cavity 707 that receives the IOL 110. As illustrated, the IOL 110 is disposed in cavity 707 formed in the housing 702.

The arms 704 are pivotably attached to the housing 702 and pivot about respective axes 709. In some instances, the axes 709 may be parallel to an optical axis 690 of the optic 114. In other implementations, the axes 709 may have other orientations relative to the optic 114. The edge rollers 706 are pivotably received in the housing 702. The edge rollers 706 pivot on pins (not shown) about axes 715 (e.g., shown on FIG. 10). Each of the arms 704 engages one of the haptic extensions 112. When actuated (described in more detail below), the arms 704 cause the haptic extensions 112 to fold over and onto the optic 114. The edge rollers 706 receive lateral edges of the optic 114 into a groove formed in each of the respective edge rollers 706, described in more detail below. When actuated, the edge rollers 706 pivot about respective axes (e.g. axes 1005 on FIG. 10) inwardly such that the optic 114 folds into a U-shape. In some instances, the arms 704 are operated first to fold the haptic extensions 112 over the optic 114, and the edge rollers 706 are operated after operation of the arms 704 such that the optic 114 folds over and captures the haptic extensions 112, thereby placing the IOL 110 in a folded configuration, such as the folded IOL 116 shown in FIG. 1.

Each of the arms 704 includes a tab 717 extending therefrom. The tabs 717 may be utilized to rotate the arms 704 about the axes 709. In some instances, a user may engage the tabs 717 to actuate the arms 704. In other instances, include a device, mechanism, or system may be utilized to actuate the arms 704. An example cam device is described in detail below with respect to another example haptic optic management system that is used to actuate the arms and other components of the example haptic optic management system.

Figure 9:
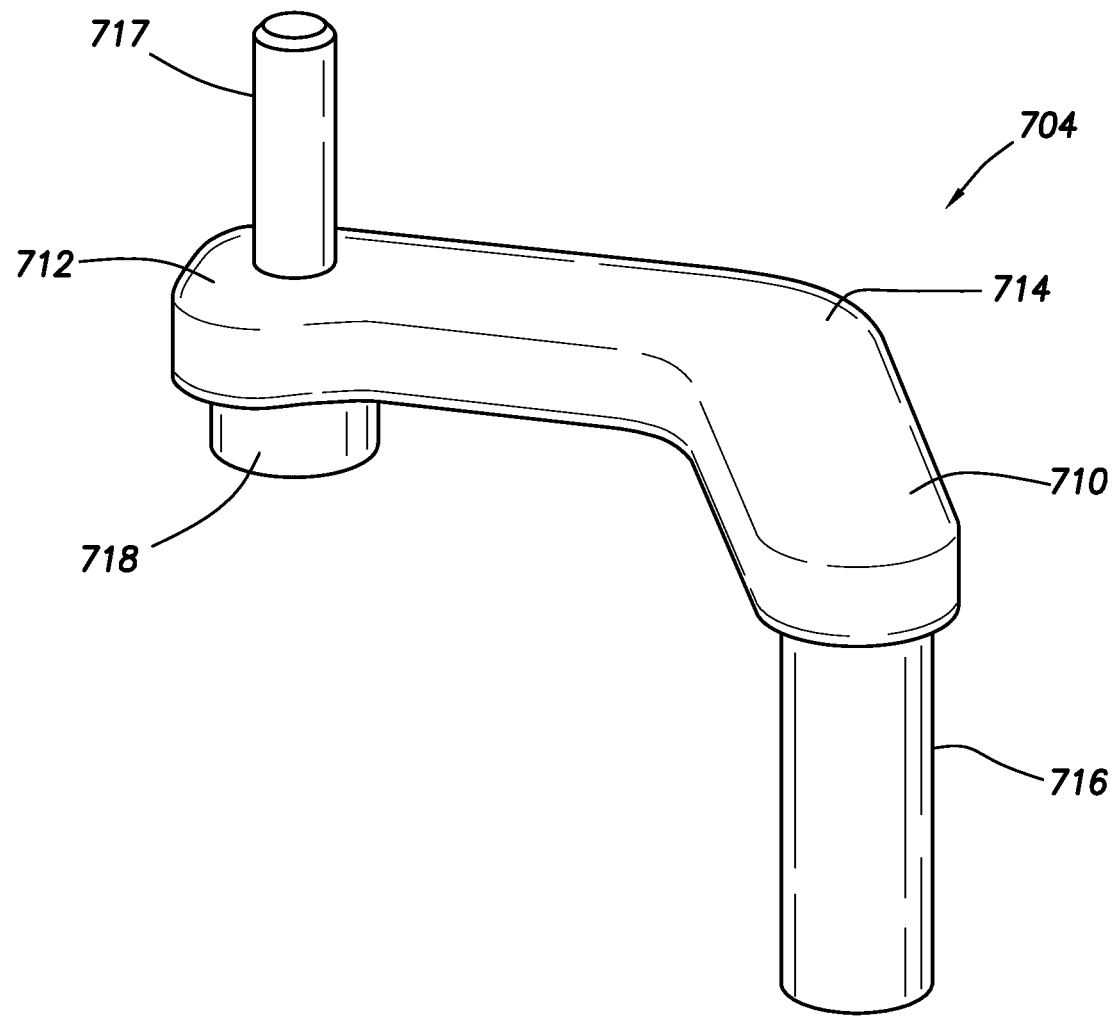
FIG. 9 illustrates an arm of the example haptic optic management system of FIG. 7.

With additional reference to FIG. 9, a perspective view of one of arms 704 is shown. There may be a plurality of arms 704. The arm 704 may be made from any suitable material. Suitable materials may include, but are not limited to, metals, nonmetals, polymers, ceramics, and/or combinations thereof. The arm 704 may be any suitable size, height, and/or shape. Without limitation, a suitable shape may include, but is not limited to, cross-sectional shapes that are circular, elliptical, triangular, rectangular, square, hexagonal, and/or combinations thereof.

In the illustrated embodiment, the arm 704 includes a first portion 710 and second portion 712. The first portion 710 and the second portion 712 join at a bend 714. A pin 716 extends from the second portion 712. The pin 716 is received into a bore formed in the housing 702 (e.g., bore 826 shown on FIG. 8), and the arm 704 pivots about the pin 716. The tab 717 extends from the second portion 712 on a side of the arm opposite the pin 716. As explained above, the tab 717 may be used to actuate the arm 704 so as to pivot the arm 704 about the pin 716. Any suitable technique may be used to apply the external force to the tab 717. In embodiments, an operator (not shown) may grip and turn the tab 717 thereby causing the entire arm 704 to rotate about the pin 716. The arm 704 also includes a protrusion 718 extending from second portion 712 on a side thereof opposite the tab 717. The protrusion 718 is operable to engage a haptic extension 112 of an IOL 110 to fold the haptic extension 112 during actuation of the HOMS 106.

Figure 10:
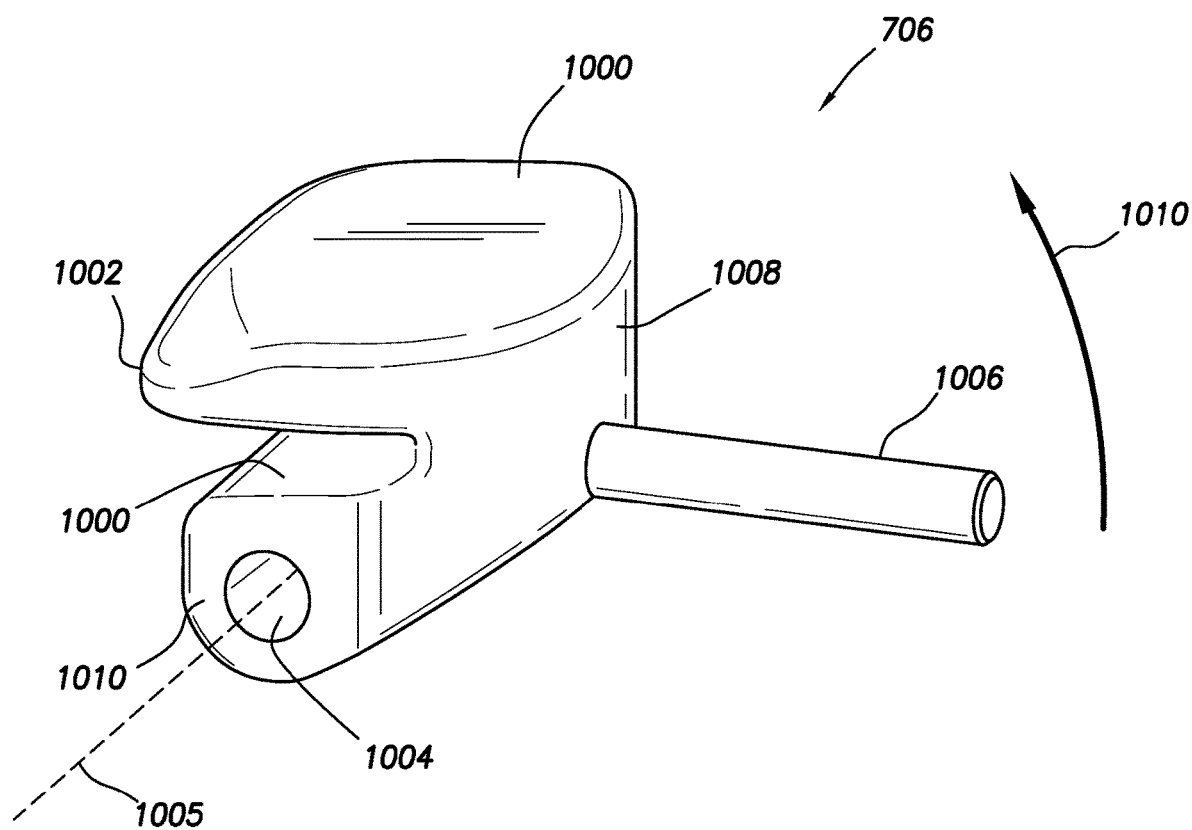
FIG. 10 illustrates an edge roller of the example haptic optic management system of FIG. 7.

With additional reference to FIG. 10, a perspective view of the edge roller 706 is shown. There may be a plurality of edge rollers 706. The edge roller 706 may be made from any suitable material. Suitable materials may include, but are not limited to, metals, nonmetals, polymers, ceramics, and/or combinations thereof. The edge roller 706 may be any suitable size, height, and/or shape. In the illustrated embodiment, the edge roller 706 includes a slot 1000 formed in a first surface 1002. The slot 1000 is adapted to receive a portion of an optic of an IOL, such as the optic 114 of IOL 110. The edge roller 706 also includes a bore 1004 formed adjacent to the slot 1000. When installed in the housing 702, the bore 1004 aligns with the bore 838 (e.g., best seen on FIG. 8) formed in the housing 702. While not shown, a pin (not shown) may extend through aligned bores 1004 and 838 for securing the edge roller 706 in the housing 702, such that the edge roller 706 pivots about axis 715. A tab 1006 extends from a side 1008 opposite the first surface 1002. The tab 1006 may be utilized to rotate the edge roller 706 about the bore 1004. In some instances, a user may engage the tab 1006 to actuate the edge roller 706, thereby causing the edge roller 706 to pivot about the bore 1004 in the direction of arrow 1010. In other instances, include a device, mechanism, or system may be utilized to actuate the edge rollers 706. An example cam device is described in detail below with respect to another example haptic optic management system that is used to actuate the arms and other components of the example haptic optic management system.

Figure 8:
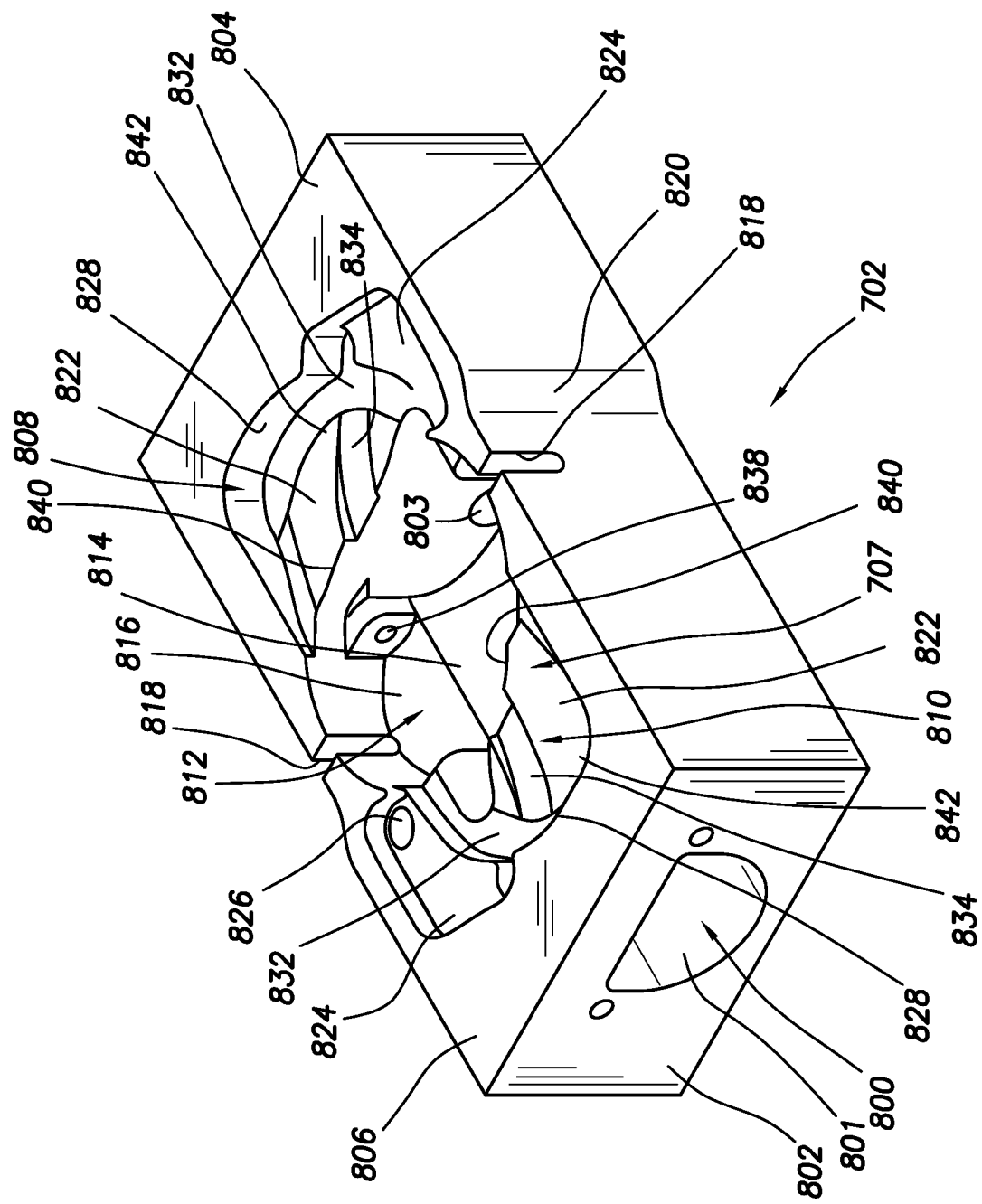
FIG. 8 illustrates a lens bay of the haptic optic management system of FIG. 7.

With additional reference to FIG. 8, the housing 702 is illustrated in more detail. The housing 702 may be made from materials, such as, for example, metals, nonmetals, polymers, ceramics, and/or combinations thereof. The housing 702 may have any size and/or shape. For example and without limitation, the housing 702 may be shaped such that all or a portion of the housing 702 may have a cross-sectional shape that is circular, elliptical, triangular, rectangular, square, hexagonal, and/or combinations thereof. In other embodiments, all or a portion of the housing 702 may have a rectangular cross-sectional shape.

The housing 702 includes a bore 800 that traverses an entire length of the housing 702 from a first end 802 of the housing 702 to a second end 804 of the housing 702. The bore 800 defines a path through which a plunger (e.g., plunger 104 shown on FIG. 1) advances to engage an IOL 110 and drive the IOL 110 through the HOMS 106. In some implementations, the plunger continues to drive the IOL 110 through the nozzle of the insertion tool and expel the IOL 110 from the insertion tool. In the example shown in FIG. 8, a first portion 801 of the bore 800 extending distally from the cavity 707 formed in the housing 702 has a U-shaped cross-section. However, the scope of the disclosure is not so limited. In other implementations, the bore 800 may have a cross-sectional shape that is circular, oval, rectangular, square, triangular, polygonal, or any other cross-sectional shape. A second portion 803 of the bore 800 has a smaller cross-sectional size than that of the first portion 801. Further, the cross-sectional shape of the second portion 803 is different than that of the first portion 801. Particularly, as shown in FIG. 8, the second portion 803 has a circular cross-sectional shape. However, other cross-sectional shapes and sizes of the first portion 801 and second portion 803, such as those described above, are within the scope of the present disclosure. Further, in some instances, the cross-sectional sizes and shapes of the first portion 801 and the second portion 803 may be the same. The cross-sectional size of the second portion 803 may be smaller from that of the first portion 801 because the second portion 803 may be used to pass the plunger, which generally has a smaller size than a folded IOL.

The cavity 707 is formed in a first surface 806 of the housing 702 and receives an IOL 110 there into. In some embodiments, there may be a portion, or portions, of material missing from the first surface 806 to form the cavity 707. The first surface 806 may be any suitable side of the housing 702. In the illustrated embodiment, the first surface 806 may be formed in any suitable side of the housing 702. In the illustrated embodiment, the first surface 806 with the cavity 707 may be the top side of the housing 702.

The cavity 707 includes a first end portion 808, a second end portion 810, and a central portion 812. The central portion 812 is deeper than the first end portion 808 and the second end portion 810 in that the central portion 812 extends a greater distance into the housing 702. An IOL 110 is received into the cavity 707 of the housing 702 such that the optic 114 of the IOL 110 is suspended over the central portion 812. A base 814 of the central portion 812 may conform to that of the bore 800. Thus, in the illustrated example, the base 814 has a cross-sectional shape that is U-shaped. The central portion 812 also includes platforms 816 laterally offset from the base 814. One of the platforms 816 is obstructed in FIG. 8 by a portion of the housing 702. The platforms 816 are raised relative to the base 814 but are recessed below the first end portion 808 and the second end portion 810. Slots 818 are formed in sidewalls 820. The slots 818 are adapted to receive the tabs 1006 of the edge rollers 706.

Each of the first end portion 808 and the second end portion 810 includes an inclined surface 822, a raised platform 824, a bore 826 formed in the raised platform 824, and an end wall 828. The end walls 828 have an arcuate shape that conforms to curvature of the haptic extensions 112 of an IOL 110. The curvature of the end walls 828 assists in keeping the IOL 110 retained within the housing 702 in a desired orientation. In other implementations, the end walls 828 may have other shapes. For example, the shape of the ends walls 828 a non-arcuate shape that conforms to a non-arcuate shaped haptic. In still other implementations, the end walls 828 may have a shape that does not correspond or otherwise conform to a shape of the haptic extensions 112 of an IOL 110. The end walls 828, in combination with the raised platforms 824 form recesses 830. The arms 704 may be at least partially received on the raised platforms 824 when the arms 704 are in an unactuated condition.

Portions 832 of the first end portion 808 and the second end portion 810, disposed between the ends walls 828 and the inclined surfaces 822, define recesses that receive the haptics of an IOL (e.g., haptic extensions 112 of IOL 110 shown on FIG. 7) when the IOL 110 is in an unstressed condition. The portions 832 assist in positioning the IOL 110 disposed within the cavity 707 of the housing 702 in a desired orientation. As illustrated, the portions 832 may be arcuate in shape, but the portions 832 may be otherwise formed as desired for a particular application. The arms 704 are supported by the raised platforms 824, with the pins 716 of the arms 704 received into the bores 826. As mentioned above, the arms 704 are pivotable about the pins 716 within the bores 826. The inclined surfaces 822 operate to lift the haptics of an IOL over the optic as the haptics are displaced by the arms 704. The inclined surfaces 822 may be disposed on at any suitable position on the respective first end portion 808 and second end portion 810 and may be set at any suitable angle. As illustrated in FIG. 8, the inclined surfaces 822 include a groove 834 that conforms to a path traveled by the protrusions 718 of the arms 704 as the arms 704 are pivoted on the pins 716 about axes 709. As further illustrated, a first end 840 of inclined surfaces 822 may tangentially align with the central portion 812 of the cavity 707. A second end 842 of the inclined surfaces 822 may be adjacent to the portions 832.

The edge rollers 706 are received within the central portion 812 of the cavity 707 on the platforms 816. Bores 838 in the housing 702 may be aligned with the bores 713 in the edge rollers 706. As explained above, pins (not shown) extend through the aligned bores 1004 of the edge rollers 706 and the bores 713 formed in the housing 702 such that the edge rollers are pivotable on the pins about axes 715. The tabs 1006 of the edge rollers 706 are received in the slots 818. In an unactuated position, the tabs 1006 rest on a closed end 836 of the slots 818. In an unactuated position, the tabs 1006 of the edge rollers 706 may be perpendicular to the sidewalls 820. However, in other implementations, the tabs 1006 may be disposed at other orientations relative to the sidewalls 820. With the edge rollers 706 installed in the housing 702, lateral edges of an IOL installed in the cavity 707 are received into the slots 1000 formed in the edge rollers 706.

With reference now to FIGS. 7 and 11-13, operation of the haptic management system 106 in operation will now be described in more details. As illustrated by FIG. 7, an operator may place the IOL 110 into the housing 702. In the illustrated embodiment, the IOL 110 may be disposed in the cavity 707 in order to pre-load the haptic optic management system 106. The IOL 110 may be placed into the cavity 707 in a relaxed or initial state, wherein the haptic extensions 112 extend from the optic 114. The haptic extensions 112 may be disposed on the portions 832 of the cavity 707. At least a portion of the edges 719 of the IOL 110 may be held by the edge rollers 706. As illustrated, at least a portion of the edges 719 of the IOL 110 may be disposed within the slot 1000 of the edge roller 706. In the illustrated embodiment, the edge rollers 706 may secure the IOL 110 over the central portion 812 (e.g., shown on FIG. 8) of the cavity 707.

Figure 11:
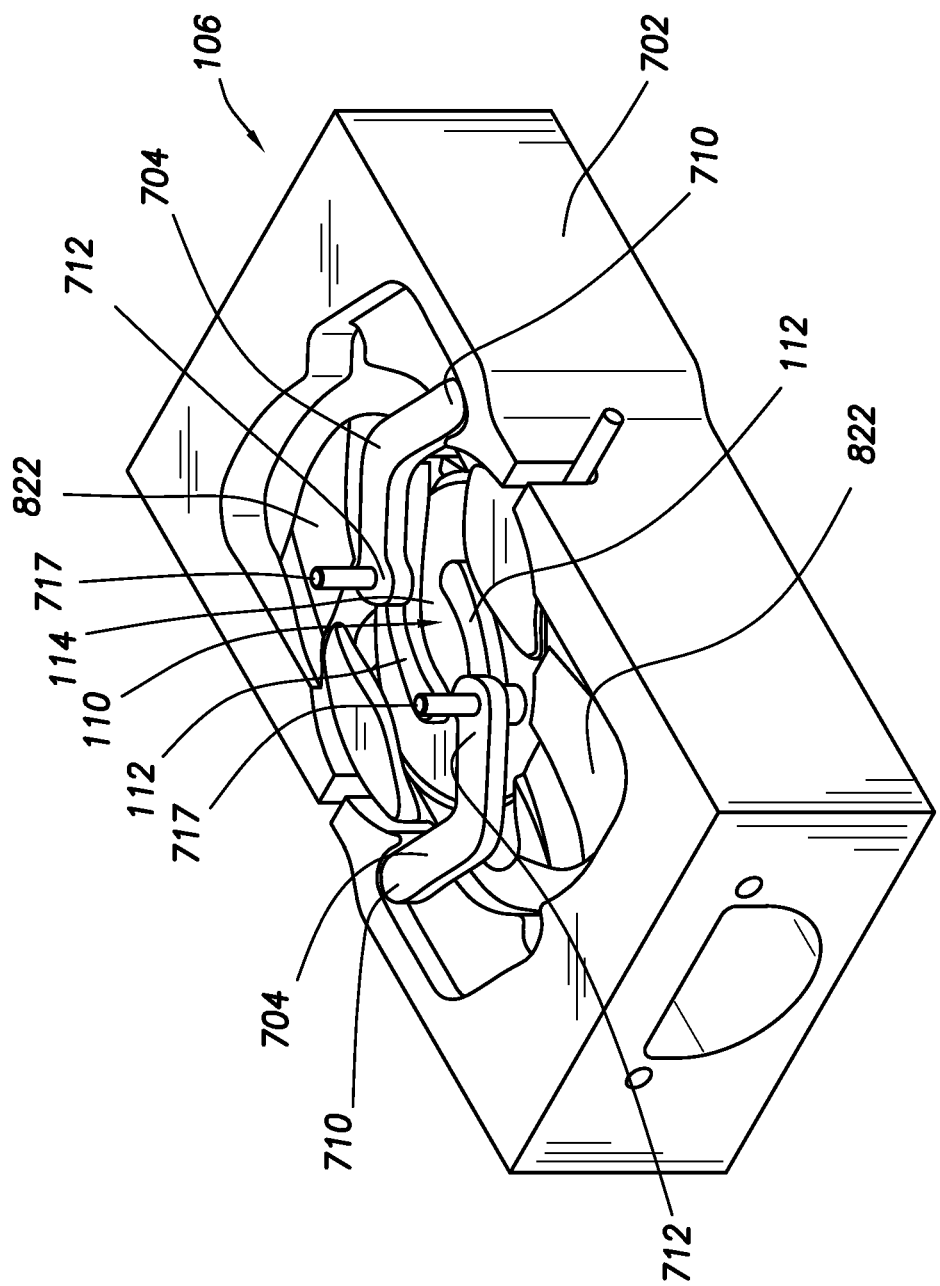
FIG. 11 illustrates the haptic optic management system of FIG. 7 in which the arms are in an actuated position during operation thereof.

FIG. 11 illustrates actuation of the arms 704 to move the haptic extensions 112 onto the optic 114 of the IOL 110 in accordance with present embodiments. As previously described, embodiments may include application of a force onto tabs 717 of the arms 704 to cause the arms 704 to rotate about the first portion 710 of the arms 704. As the force causes the arms 704 to rotate and move, the arms 704 may engage the haptic extensions 112 of the IOL 110 causing them to move up the included surfaces 822. In embodiments, the arms 704 may fold the haptic extensions 112 on top of and over the optic 114. In the illustrated embodiment, the second portion 712 of the arms 704 may engage the haptic extensions 112 moving the haptic extensions 112 along the inclined surfaces 822 of the housing 702. As the haptic extensions 112 move along the inclined surfaces 822, the haptic extensions 112 move upward such that the haptic extensions 112 may move off the inclined surfaces 822 and on top of the optic 114 of the IOL 110.

Figure 12:
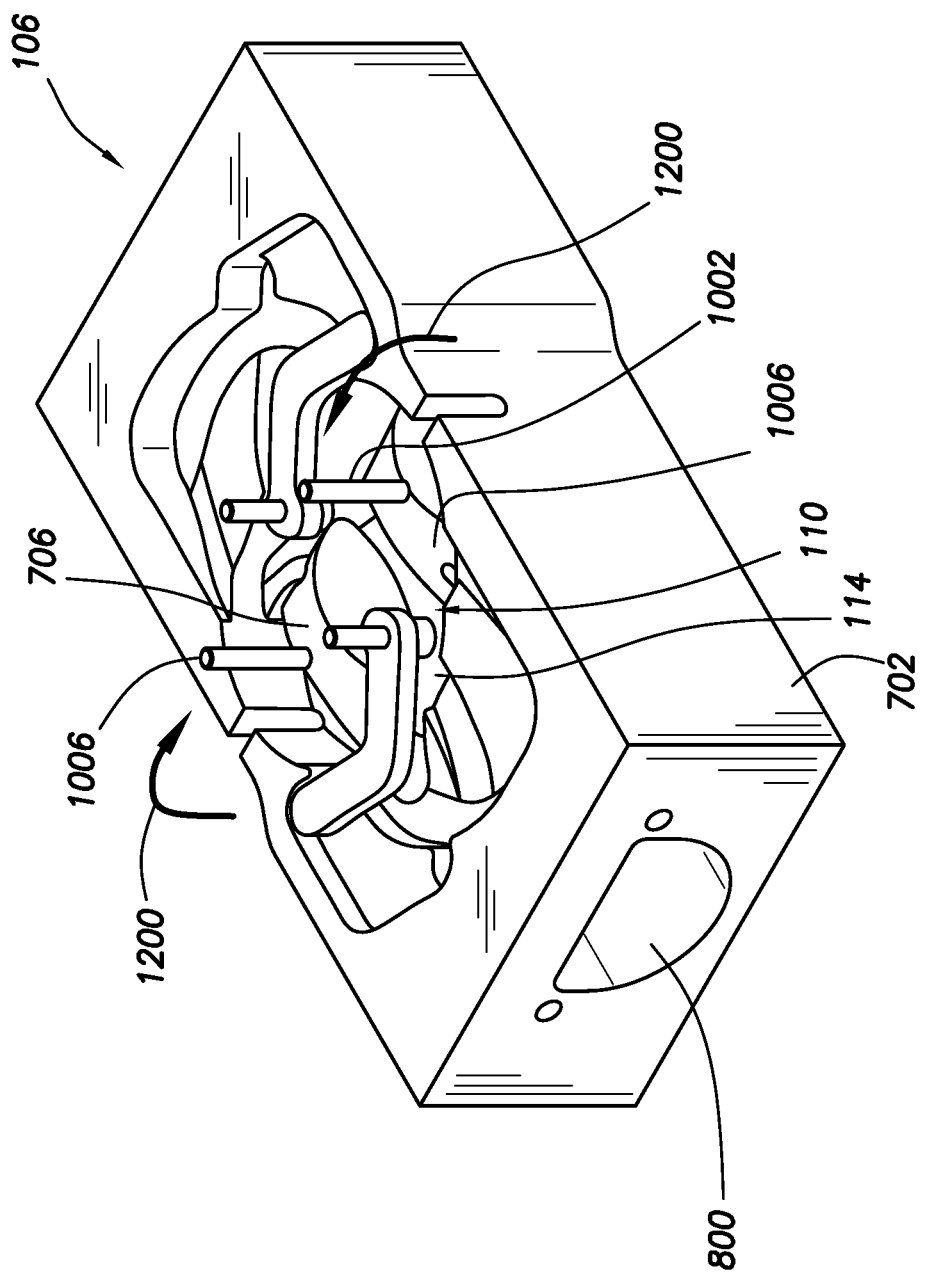
FIG. 12 illustrates the haptic optic management system of FIG. 7 in which the arms and the edge rollers are in an actuated position during operation thereof.

FIG. 12 illustrates actuation of the edge rollers 706 to fold the IOL 110 in accordance with present embodiments. As previously described, embodiments may include application of a force to the tabs 1106 of the edge rollers 706 causing the edge rollers 706 to each pivot in arc 1200. As the force causes the edge rollers 706 to pivot, the optic 114 of the IOL 110 may be forced to fold in upon itself as the optic 114 may be at least partially disposed in the slot 1000 (e.g., referring to FIG. 10) of the edge rollers 706. In addition, pivoting of the edge rollers 706 in the arc 1200 may move the IOL 110 into the bore 800 formed in the housing 702.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A haptic optic management system, comprising:
 a housing comprising a bore and a cavity disposed in a first surface of the housing, wherein the cavity comprises a first end portion, a second end portion, and a central portion, and wherein the cavity provides access to the bore through the first surface of the housing;
 a plurality of arms coupled to the housing, wherein the plurality of arms comprises a first arm disposed in the first end portion and a second arm disposed in the second end portion, and wherein each of the plurality of arms comprises:
 a first portion,
 a second portion joined to the first portion at a bend,
 a pin extending from the first portion, and
 a tab extending from the second portion; and
 edge rollers coupled to the housing.

2. The haptic optic management system of claim 1, wherein the bore comprises a first portion that has a U-shaped cross-section and extends from a first end of the housing to the central portion of the cavity, and wherein the bore comprises a second portion that has a smaller cross-section than the first portion and extends from the central portion of the cavity to a second end of the housing.

3. The haptic optic management system of claim 1, further comprising an intraocular lens disposed in the cavity, wherein the intraocular lens comprises an optic and haptic extensions that extend from the optic.

4. The haptic optic management system of claim 3, wherein one of the haptic extensions extends from the optic onto the first end portion, and wherein another of the haptic extensions extends from the optic onto the second end portion.

5. The haptic optic management system of claim 1, wherein the first end portion and the second end portion each comprises an end wall, a raised platform adjacent to the end wall for supporting one of the arms, a portion adjacent to the raised platform for supporting a haptic extension of an intraocular lens, and an inclined surface adjacent to the portion.

6. The haptic optic management system of claim 1, wherein each of the plurality of arms is rotatable about the respective first portion.

7. The haptic optic management system of claim 1, wherein the edge rollers comprises a pair of the edge rollers, wherein each of the pair of the edge rollers are disposed on opposite platforms formed on either side of the central portion of the cavity.

8. The haptic optic management system of claim 1, wherein the edge rollers each comprise a slot formed in a first surface for receiving an edge of an optic of an intraocular lens, a bore formed adjacent the slot, and a tab extending on a second surface opposite the first surface, wherein the tab is received in a slot formed in a sidewall of the housing.

9. The haptic optic management system of claim 8, wherein the tab is received in a slot formed in a sidewall of the housing.

* * * * *